(12) United States Patent
Moumene et al.

(10) Patent No.: US 8,043,379 B2
(45) Date of Patent: Oct. 25, 2011

(54) DISC PROSTHESIS HAVING REMOTE FLEXION/EXTENSION CENTER OF ROTATION

(75) Inventors: Missoum Moumene, Newton, MA (US); Martin Masson, Raynham, MA (US)

(73) Assignee: DePuy Spine, Inc., Raynham, MA (US)

( * ) Notice: Subject to any disclaimer, the term of this patent is extended or adjusted under 35 U.S.C. 154(b) by 298 days.

(21) Appl. No.: 11/408,854

(22) Filed: Apr. 21, 2006

(65) Prior Publication Data
US 2007/0250170 A1 Oct. 25, 2007

(51) Int. Cl.
*A61F 2/44* (2006.01)
(52) U.S. Cl. .................. 623/17.15; 623/17.14
(58) Field of Classification Search .............. 623/17.14, 623/17.15, 17.16, 17.11–17.13; 606/246, 606/249
See application file for complete search history.

(56) References Cited

U.S. PATENT DOCUMENTS

| | | | | |
|---|---|---|---|---|
| 6,679,915 | B1 * | 1/2004 | Cauthen | 623/17.11 |
| 7,048,764 | B2 * | 5/2006 | Ferree | 623/17.15 |
| 7,235,104 | B2 * | 6/2007 | Grinberg et al. | 623/17.14 |
| 7,637,955 | B2 * | 12/2009 | Marik et al. | 623/17.14 |
| 2003/0176923 | A1 | 9/2003 | Keller et al. | |
| 2004/0117022 | A1 | 6/2004 | Marnay et al. | |
| 2004/0143332 | A1 * | 7/2004 | Krueger et al. | 623/17.14 |
| 2004/0215342 | A1 * | 10/2004 | Suddaby | 623/17.12 |
| 2005/0033438 | A1 * | 2/2005 | Schultz et al. | 623/17.15 |
| 2005/0154468 | A1 * | 7/2005 | Rivin | 623/17.16 |
| 2005/0187633 | A1 * | 8/2005 | Ferree | 623/17.15 |
| 2005/0216092 | A1 * | 9/2005 | Marik et al. | 623/23.39 |
| 2005/0256577 | A1 * | 11/2005 | Baumgartner et al. | 623/17.15 |
| 2005/0283242 | A1 * | 12/2005 | Zucherman et al. | 623/17.15 |
| 2006/0009850 | A1 * | 1/2006 | Frigg et al. | 623/17.13 |
| 2006/0036326 | A1 * | 2/2006 | Baumgartner et al. | 623/17.15 |
| 2006/0212123 | A1 * | 9/2006 | Lechmann et al. | 623/17.15 |
| 2006/0235528 | A1 * | 10/2006 | Buettner-Janz | 623/17.14 |
| 2006/0247777 | A1 * | 11/2006 | Stamp | 623/17.14 |
| 2007/0083267 | A1 * | 4/2007 | Miz et al. | 623/17.13 |
| 2007/0100453 | A1 * | 5/2007 | Parsons et al. | 623/17.14 |
| 2008/0234686 | A1 * | 9/2008 | Beaurain et al. | 606/90 |

FOREIGN PATENT DOCUMENTS

WO WO 02089701 A2 * 11/2002
WO WO 2004/054480 7/2004

* cited by examiner

*Primary Examiner* — Eduardo C Robert
*Assistant Examiner* — Jan Christopher Merene
(74) *Attorney, Agent, or Firm* — Maginot, Moore & Beck

(57) ABSTRACT

An intervertebral disc prosthesis comprises a first endplate, a second endplate, and a bearing surface positioned between the first endplate and the second endplate. The bearing surface may be provided by a mobile bearing disc including a convex bearing surface configured to engage the first endplate and a concave bearing surface configured to engage the second endplate. The multiple bearing surfaces of the mobile bearing disc engage articulating surfaces on the endplates to form a plurality of articulating joints. Each articulating joint is configured to facilitate a particular type of movement for the segmental unit. Furthermore, each articulating joint is defined by a distinct center of rotation. The contact pair formed by the convex bearing surface of the bearing component and the concave bearing surface of the first endplate may provide a flexion/extension center of rotation for the prosthesis. The contact pair formed by the convex bearing surface of the bearing component and the concave bearing surface of the first endplate may provide a lateral bending/torsional center of rotation for the prosthesis.

20 Claims, 7 Drawing Sheets

DISC PROSTHESIS HAVING REMOTE FLEXION/EXTENSION CENTER OF ROTATION

BACKGROUND

This invention relates to the field of prosthetics, and more particularly, to an intervertebral disc prosthesis designed to replace a damaged intervertebral disc.

The human spine consists of twenty-four small bones known as vertebrae that protect the spinal cord and provide stability to the torso. The vertebrae are arranged in a column and stacked vertically upon each other. Each vertebra is comprised of two parts including an anterior part and a posterior part. The anterior part is often referred to as the vertebral body, and the posterior part is often referred to as the vertebral arch. The vertebral bodies are generally separated by a fibrous bundle of tissue called an intervertebral disc. These intervertebral discs act as a cushion to the spinal column by absorbing energy and transmitting loads associated with everyday movement. They also prevent the vertebrae from rubbing against each other. The combination of an intervertebral disc and its associated superior vertebra and inferior vertebra may be referred to as a functional segmental unit.

Over time, the normal aging process causes the intervertebral discs to degenerate, diminishing their water content and thereby reducing their ability to properly absorb the impact associated with spinal movements. Diminished water content in the intervertebral discs may also cause the vertebrae to move closer together. Tears and scar tissue can weaken the discs, resulting in injury. When the discs wear out or are otherwise injured, a condition known as degenerative disc disease results. With this condition, discs do not function normally and may cause pain and limit activity.

The condition of degenerative disc disease can potentially be relieved by a surgical procedure called artificial disc replacement or total disc replacement. In this procedure, the damaged intervertebral disc is replaced by an intervertebral prosthetic device (i.e., an "artificial disc" or "intervertebral disc prosthesis"). A typical prior art artificial disc comprises two endplates. One endplate faces a superior vertebra and the other endplate faces an inferior vertebra. A bearing surface is provided between the two endplates, allowing the endplates to rotate relative to one another and generally mimic the motion allowed by a natural disc.

In order to be safe and efficacious, a total disc replacement should not disrupt the normal kinematics of the functional segmental unit. Preferably, an intervertebral disc prosthesis should allow the vertebra to move with respect each other by means of the same, normal, physiological, instantaneous centers of rotation as the intact functional segmental unit. Under normal conditions a superior vertebra and inferior vertebra for a given functional segmental unit will rotate with respect to each other about differing centers of rotation, depending upon the type of movement, whether flexion/extension, lateral bending, or axial rotation (also sometimes called as "torsional rotation"). Therefore, the center of rotation that defines one type of movement may be different from the center of rotation that defines another type of movement.

As noted above, the locations of instantaneous centers of rotation in the lower cervical spine depend on the type of forces exerted on the spinal segments. While the locations of these instantaneous centers of rotation have not been precisely pinpointed, general observations have been made. For example, with respect to the C5-C6 cervical functional unit, axial rotation appears to be defined by a center of rotation (COR) that is located within the disc space when viewed from above but either to the left or to the right of the geometric center of the disc, depending on the direction of motion. For flexion/extension (F/E) movement, the COR at C5-C6 is located at the anterior portion of the subsequent, lower vertebra. In lateral bending, there is much speculation about the region of interest for determining the instantaneous centers of rotation. However, it appears that lateral bending is defined by a COR near the geometric center of the disc, which varies depending on the direction of motion.

Contemporary cervical intervertebral prosthetic devices typically have a COR that is centrally located immediately below a single contacting surface radius. While this may allow relatively normal lateral bending and axial rotation, such a design does not take into account the normal flexion-extension COR located at the anterior portion of the subsequent, lower vertebra. As far as flexion-extension is concerned, a central COR is not consistent with the normal kinematics of the functional segmental unit. Accordingly, a central COR for flexion/extension movements will force the vertebrae along non-physiologic paths.

As a vertebra goes through its ranges of motion, the pattern of motion is determined by a combination of the physical contact between the geometric anatomy of the structures, their physical properties, and the properties of the passive restraints that hold the functional units together (ligaments, muscles, etc.). The facets are the anatomical features that contribute most to dictating where the center of motion will be located. In the C5-C6 region, the facets are positioned approximately at a 45 degree angle to the disc. This is an important clue as to an anterior location for the flexion/extension COR. Thus, the centrally located COR typically found in current prosthetic discs is inconsistent with the plane of the contacting facets at the C5-C6 level.

Accordingly, it would be advantageous to provide a total disc replacement that performs consistent with the normal kinematics of the functional segmental unit. Furthermore, it would be advantageous to provide an intervertebral disc prosthesis configured to provide multiple, adaptative centers of rotation, depending upon the type of vertebral movement facilitated by the disc, including one center of rotation substantially removed from another center of rotation.

SUMMARY

An intervertebral disc prosthesis having a plurality of independent centers of rotation is disclosed herein. One of the centers of rotation is a flexion/extension center of rotation that is remote from another center of rotation. The intervertebral disc prosthesis is configured for insertion between a superior vertebral body and an inferior vertebral body in a patient.

The intervertebral disc prosthesis comprises a first endplate, such as a superior endplate, including a first vertebra facing surface and a concave articulating surface. The intervertebral disc prosthesis also comprises a second endplate, such as an inferior endplate, including a second vertebra facing surface and a convex articulating surface. A mobile bearing disc is positioned between the first endplate and the second endplate. The mobile bearing disc includes a convex bearing surface configured to engage the concave articulating surface of the first endplate and a concave bearing surface configured to engage the convex articulating surface of the second endplate.

The multiple bearing surfaces of the mobile bearing disc engage the articulating surfaces of the endplates to form a plurality of articulating joints (also referred to as "contact pairs"). Each articulating joint is configured to facilitate a particular type of movement for the segmental unit. Furthermore, each articulating joint is defined by a distinct center of rotation. In one embodiment, the contact pair formed by the concave bearing surface of the bearing component and the convex bearing surface of the second endplate is configured to provide a flexion/extension center of rotation for the prosthesis. This flexion/extension center of rotation may be located on an anterior portion of the inferior vertebra. In one embodiment, the flexion/extension center of rotation is located outside of the space directly beneath the concave bearing surface of the bearing component.

While the contact pair formed by the concave bearing surface of the bearing component and the convex bearing surface of the second endplate is configured to provide a flexion/extension center of rotation, the contact pair formed by the convex bearing surface of the bearing component and the concave bearing surface of the first endplate is configured to provide a lateral bending/torsional center of rotation for the prosthesis. In one embodiment, the lateral bending/torsional center of rotation is located directly below the convex bearing surface.

In yet another embodiment, the intervertebral disc prosthesis comprises a rail protruding and extending longitudinally across the mid section of the convex articulating surface of the inferior endplate. A mating groove for the rail is provided on the conave bearing surface of the bearing component. The rail is configured to engage the groove when the concave bearing surface of the bearing component is positioned on the convex articulating surface of the inferior endplate. In this fashion the rail and groove of this particular contact pair are configured to facilitate only flexion/extension movements. Lateral bending and axial rotation movements are prohibited by the articulating joint that include the rail and groove, and lateral bending and axial rotation movements must be facilitated by the other articulating joint. In an alternative embodiment, the rail may protrude and extend longitudinally across the mid-section of the conave bearing surface of the bearing component while a mating groove for the rail is provided along the mid-section of the convex articulating surface of the inferior endplate, thus facilitating lateral bending movements.

DESCRIPTION

Figure 1:
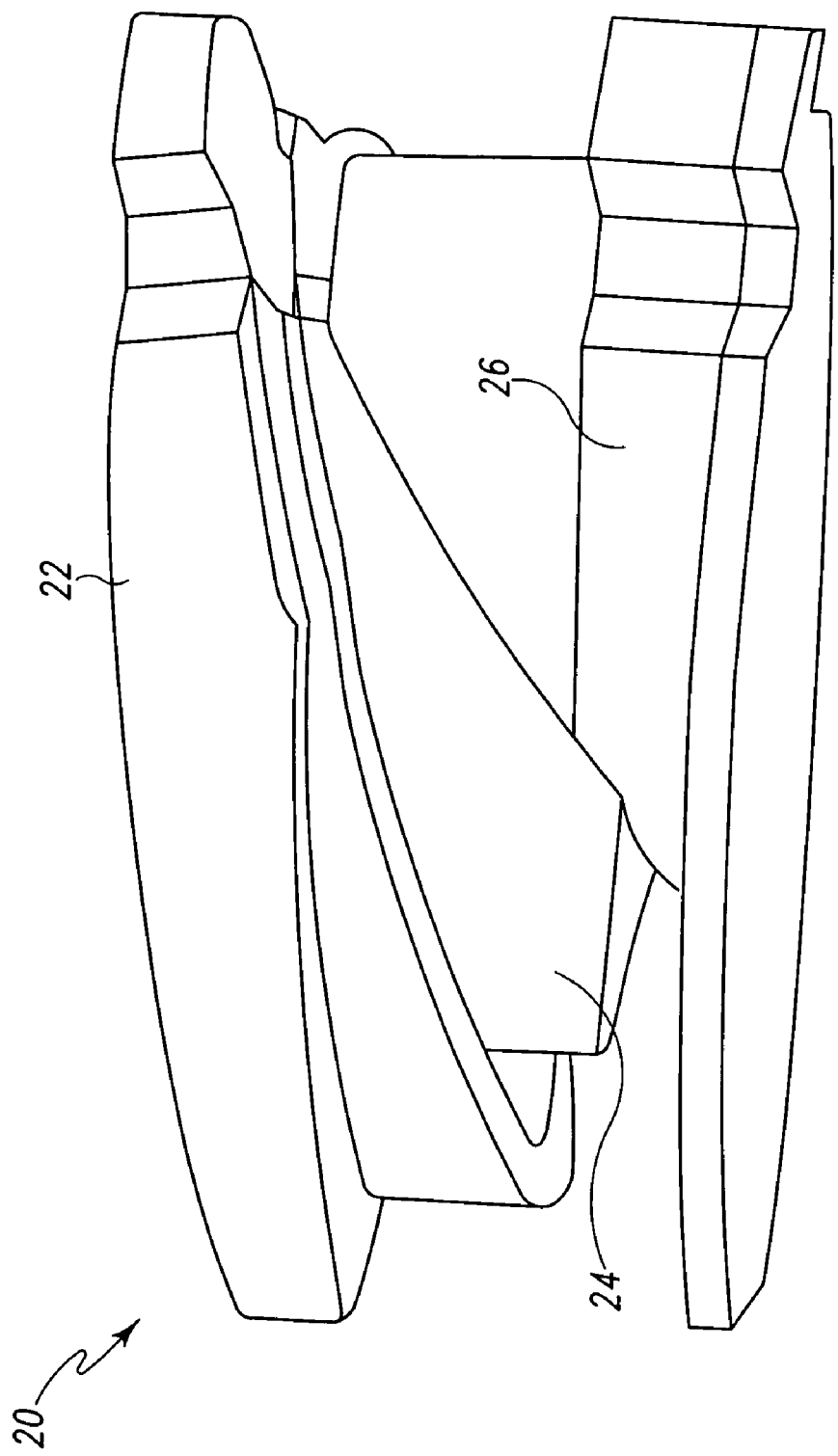
FIG. 1 shows a side perspective view of an intervertebral disc prosthesis having a remote flexion/extension center of rotation.
Figure 2:
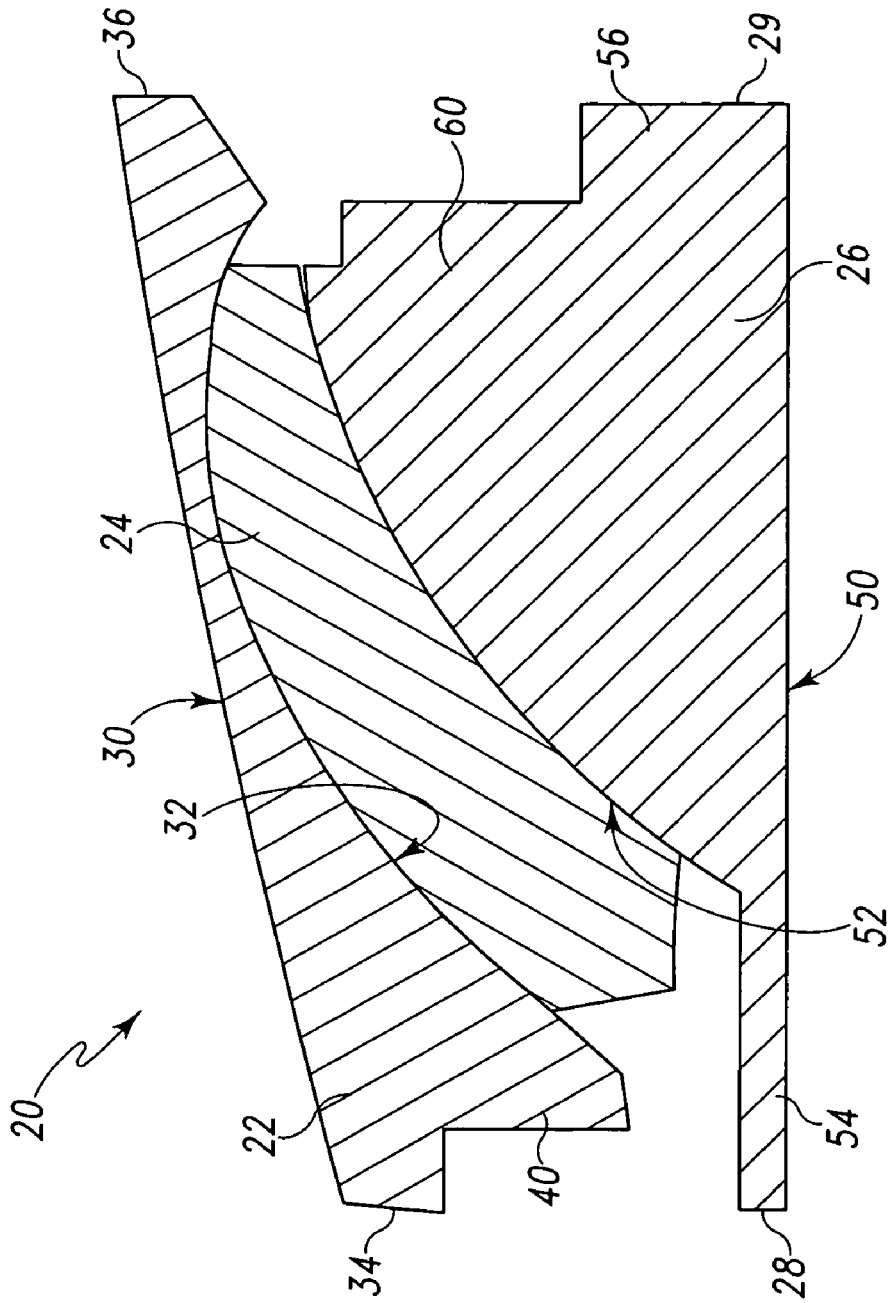
FIG. 2 shows a side cross-sectional view of the disc prosthesis of FIG. 1.

With reference to FIGS. 1 and 2, a disc prosthesis 20 having a remote flexion/extension center of rotation is shown. The disc prosthesis 20 comprises a superior endplate 22 and an inferior endplate 26 with a bearing component 24 positioned between the superior endplate 22 and the inferior endplate 26. The superior plate 22 engages the bearing component 24 and is configured to rotate upon the bearing component 24. Likewise, the inferior plate 26 engages the bearing component 24 and is configured to rotate upon the bearing component 24.

Figure 3:
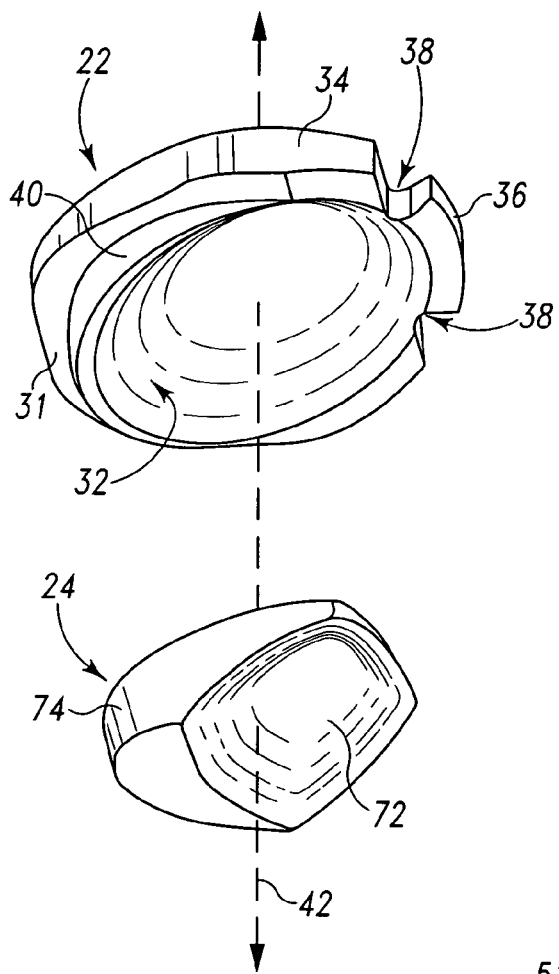
FIG. 3 shows a lower perspective view of a superior plate and mobile bearing of the disc prosthesis of FIG. 1 positioned along a central axis.

The superior plate 22 may be comprised of a metal material such as a medical grade cobalt chromium alloy. With reference generally to FIGS. 2 and 3, the superior plate 22 generally is generally disc shaped and includes an upper surface 30 and a lower articulating surface 32. The upper surface 30 is configured to engage a superior vertebra in a patient. To this end, the upper surface includes fixation devices (not shown), such as a keel or teeth designed to penetrate the surface of the superior vertebra. A sidewall 34 extends around the perimeter of the superior plate 22, defining a footprint for the plate. A tab 36 is formed on the anterior portion. The tab 36 is flanked by two notches 38. The notches 38 are configured to receive the arms of a disc insertion tool (not shown), such that the disc may be easily grasped with the disc insertion tool.

The lower articulating surface 32 is formed on the bottom side 31 of the plate 22 opposite the upper vertebra facing surface 30. The lower articulating surface 32 is concave and forms a substantially semi-spherical surface designed to engage the bearing component 24. A socket wall 40 extends downward from the bottom side 31 of the plate 22. The socket wall 40 at least partially encircles the lower articulating surface 32. The socket wall 40 may appear tilted relative to the bottom side 31 of the plate 22, depending upon the degree to which the center defining the articulating surface 32 is removed from a central axis 42.

Figure 4:
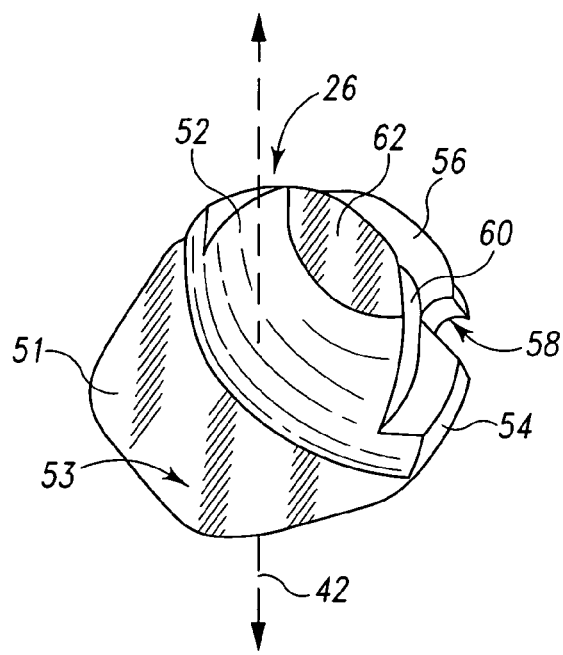
FIG. 4 shows an upper perspective view of an inferior plate relative to the central axis of FIG. 3.

Similar to the superior plate 22, the inferior plate 26 may also be comprised of a metal material such as a medical grade cobalt chromium alloy. With reference now to FIGS. 2 and 4, the inferior plate 26 comprises an upper articulating surface 52 and a lower surface 50. The lower surface 50 is configured to engage an inferior vertebra in a patient. To this end, the lower surface 50 includes fixation devices (not shown), such as a keel or teeth designed to penetrate the surface of the superior vertebra. A sidewall 54 extends around the perimeter of the superior plate 26, defining a footprint for the plate. A tab 56 is formed on the anterior portion of the plate. The tab 56 is flanked by two notches 58. The notches 58 are configured to receive the arms of a disc insertion tool (not shown), allowing the disc to be easily grasped with the disc insertion tool.

The inferior plate 26 includes an upper side 51 opposite the lower surface 50. The upper side 51 includes a generally flat surface 53 provided on a posterior portion and a dome 60 provided on an anterior portion. The dome 60 defines the upper articulating surface 52. The upper articulating surface 52 is convex and forms a substantially semi-spherical surface designed to engage the bearing component 24. The articulating surface 52 curves upward from the generally flat surface 53 until it terminates in a generally flat upper platform 62 at the peak of the dome 60. The dome appears tilted relative to the flat surface 53 of the plate 26. The degree of tilt to the dome 60 depends upon the degree to which the center defining the articulating surface 52 is removed from a central axis 42.

Figure 5:
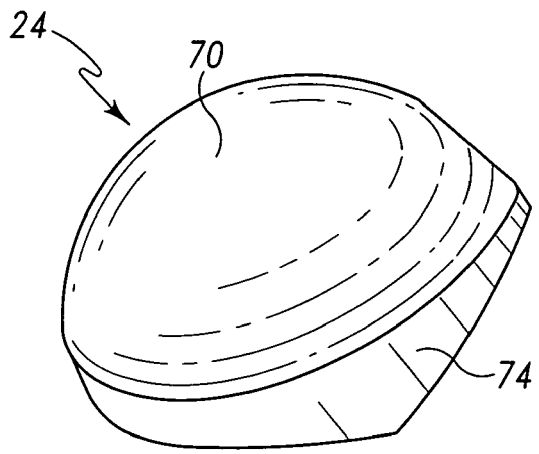
FIG. 5 shows an upper perspective view of the mobile bearing of FIG. 3.
Figure 6:
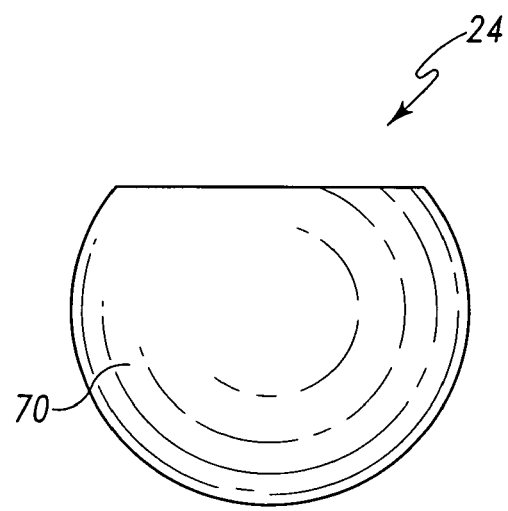
FIG. 6 shows a top view of the mobile bearing of FIG. 5.
Figure 7:
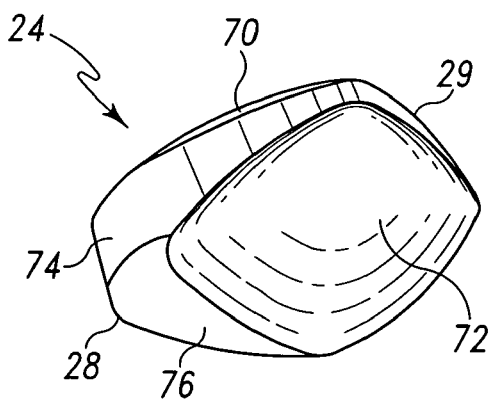
FIG. 7 shows a lower perspective view of the mobile bearing of FIG. 5.

The bearing component 24 may be comprised of an ultra high molecular weight polyethylene (UHMWPE). With reference to FIGS. 5-7, the bearing component is generally disc shaped and includes a superior bearing surface 70 on one side and an inferior bearing surface 72 on an opposite side. The superior bearing surface 70 is generally semi-spherical and is configured to be congruent with and engage the concave articulating surface 32 on the superior endplate 22. The inferior bearing surface 72 is concave and is configured to be congruent with and engage the convex articulating surface 52 on the inferior endplate 26. As best seen in FIG. 2 or FIG. 7, the inferior bearing surface 72 is tilted relative to the superior bearing surface, such that the bearing surfaces are slightly farther apart on the posterior side 28 of the component than on the anterior side 29 of the component.

A sidewall 74 is formed around the bearing component 24. The sidewall 74 is taller on the posterior portion 28 of the bearing component than on the anterior portion 29 of the bearing component. A shoulder 76 with a flat surface is provided on the lowermost anterior portion of the bearing component 24. The flat shoulder 76 is configured to engage the flat surface 53 of the inferior endplate 26 when the bearing component is rotated to an extreme posterior position on the convex articulating surface 52 of the inferior endplate 26.

When the intervertebral disc prosthesis 20 is assembled and the bearing component 24 is positioned between the superior plate 22 and the inferior plate 26, none of the bearing component's surfaces are fixed in relation to the superior plate or the inferior plate. Therefore, the three-piece construction of superior endplate, bearing component, and inferior endplate provides two articulating joints capable of independent operation. A first articulating joint is formed by the engagement of the concave articulating surface 32 on the superior plate 22 with the convex superior bearing surface 70 on the bearing component 24. A second articulating joint is formed by the engagement of the concave bearing surface 72 of the bearing component 24 with the convex articulating surface 52 of the inferior plate 26. With two articulating joints, a first center of rotation and a second center of rotation may be provided for the intervertebral disc prosthesis. These two centers of rotation are generally defined by the orientation, shape and radius of curvature of the articulating surfaces. Advantageously, by providing two centers of rotation, the first center of rotation may be used to provide an instantaneous center of rotation for one type of movement, such as axial rotation and/or lateral bending. The second center of rotation may be used to provide an instantaneous center of rotation for another type of movement, such as flexion/extension.

Figure 8:
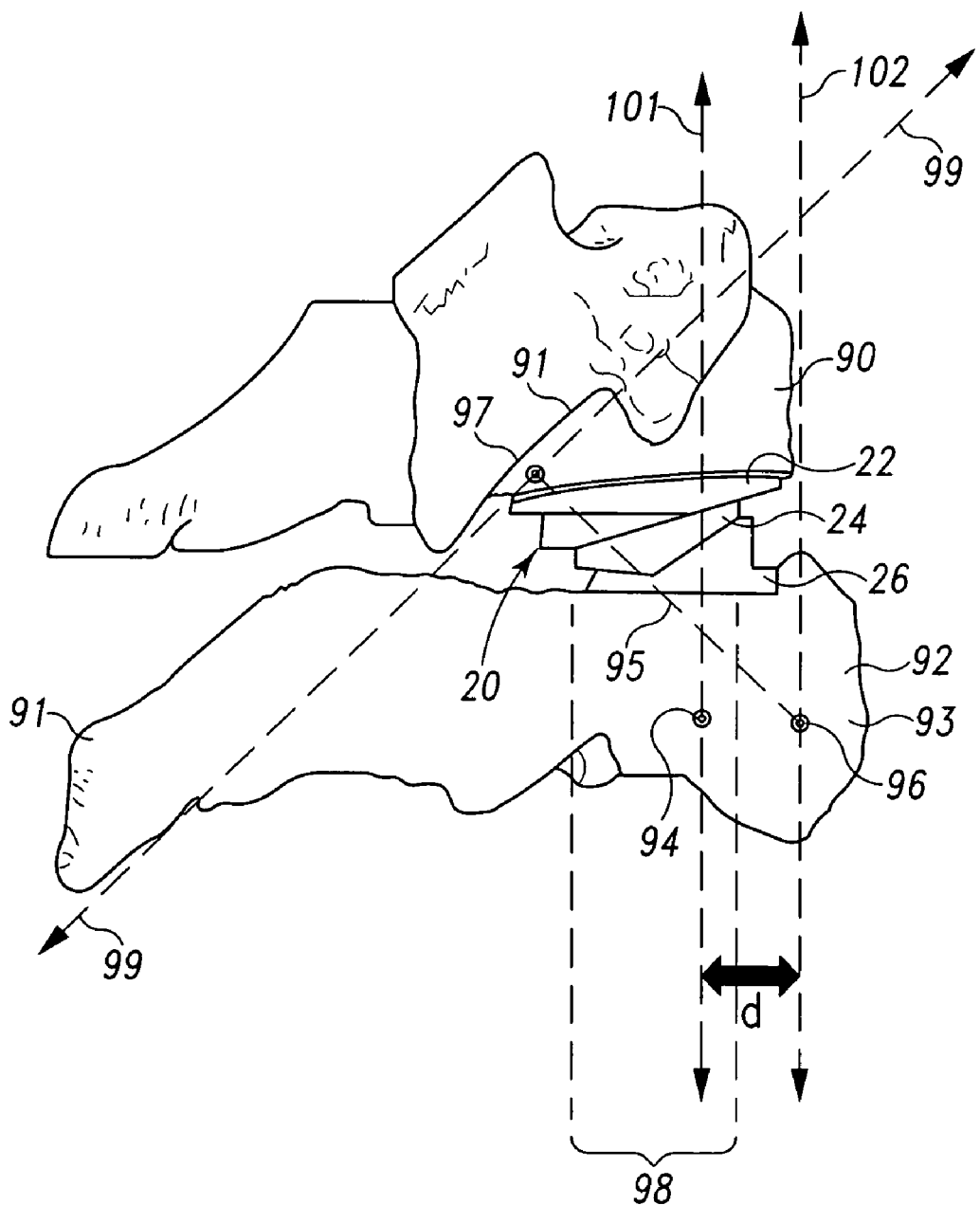
FIG. 8 shows a side view of the disc prosthesis of FIG. 1 in relation to a superior vertebra and an inferior vertebra.

With reference now to FIG. 8, an assembled intervertebral disc prosthesis 20 is shown implanted between a superior vertebra 90 and an inferior vertebra 92. The upper surface 30 of the superior plate 22 is in engagement with the superior vertebra 90 and the lower surface 50 of the inferior plate 26 is in engagement with the inferior vertebra 92.

In FIG. 8, the prosthetic device 20 is configured such that axial rotation and lateral bending is facilitated by the upper articulating joint which is provided by engagement of the concave articulating surface 32 of the superior plate 22 and the convex bearing surface 70 of the bearing component 24. Flexion/extension is facilitated by the lower articulating joint which is provided by engagement of the convex articulating surface 52 of the inferior endplate 26 and the concave bearing surface 72 of the bearing component 24.

As shown in FIG. 8, the radiuses and orientation of both the convex bearing surface 70 of the bearing component 24 and the concave articulating surface of the superior plate 22 define a first center of rotation 94 for the upper articulating joint. The first center of rotation 94 is located to the anterior portion 93 of the inferior vertebra 92, but remains within the space 98 immediately below the bearing component 24. This first center of rotation 94 provides a lateral bending/axial rotation center of rotation. In particular, during lateral bending movement, the natural forces imparted on the prosthesis by the vertebrae will encourage rotation of the superior plate 22 relative to the bearing component 24 about the first center of rotation 94.

The radiuses and orientation of both the concave bearing surface 72 of the bearing component 24 and the convex articulating surface 52 of the inferior plate 26 define a second center of rotation 96 which is for the lower articulating joint. The second center of rotation 96 is also located to the anterior portion 93 of the inferior vertebra 92, but is outside of the space 98 beneath the bearing component 24. This second center of rotation 96 provides a flexion/extension center of rotation. In particular, during flexion/extension movement, the natural forces imparted on the prosthesis by the vertebrae will encourage rotation of the inferior plate 26 relative to the bearing component 24 about the second center of rotation 96.

The second center of rotation 96 is located further on the anterior portion 93 of the inferior vertebra 92 than the first center of rotation. The first center of rotation 94 is separated from the second center of rotation 96 by a horizontal offset equal to the distance "d", which is greater than zero. The horizontal offset is the distance between a first vertical axis 101 extending through the first center of rotation 94 and a second vertical axis extending through the second center of rotation 96. In one preferred embodiment, the distance "d" is between 1 mm and 10 mm, and preferably about 5 mm.

As mentioned in the preceding paragraph, two vertical axes are shown in FIG. 8. The first vertical axis 101 passes substantially perpendicularly through the endplates 22 and 26 and vertebral surfaces of the vertebra 90 and 92 in their equilibrium positions, while also passing through the first center of rotation 94. The second vertical axis 102 is parallel to the first vertical axis and passes through the second center of rotation 96. Bracket 98 indicates the space located vertically directly beneath the bearing component 22 having boundaries parallel to vertical axis 101 and 102. When viewed from above, the first center of rotation 94 is included within this space 98, and the second center of rotation 96 is outside of this space 98.

As shown in FIG. 8, an imaginary line, represented by dotted line 95, may be drawn in the sagittal plane from the second center of rotation 96 to the center of the facet 91 of the vertebra immediately superior to the disc prosthesis 20. The center of the facet 91 is represented by point 97 in FIG. 8. This center point is generally the midpoint of the facet. An adult cervical facet is typically about 8-12 mm in diameter, so the center point is generally positioned 4-6 mm from the facet edge.

The imaginary line 95 intersects another imaginary line 99 that passes through the center 97 of the facet 91 and defines the facet angle for the vertebra. The intersection of these two imaginary lines 95 and 99 is at an angle approaching ninety degrees in the sagittal plane (e.g., and angle between 80° and 100°). Advantageously, this permits the facets to move about each other without impediment.

As explained above, the embodiment shown in FIG. 8 provides two centers of rotation for the C5-C6 cervical functional unit. The first center of rotation 94 is located at the anterior portion of the subsequent inferior vertebra 92, but remains within the space 98 directly below the core. This first center of rotation 94 is designed to provide the center of rotation for lateral bending and axial rotation movements. Accordingly, during lateral bending or axial rotation location the superior plate 22 rotates upon the bearing component 22 as the concave articulating surface 32 of the superior plate 22 engages the convex superior bearing surface 70 of the bearing component 24. The location of this center of rotation 94 as shown in FIG. 8 is consistent with current bio-medical analysis for the C5-C6 cervical functional unit.

The second center of rotation 96 is also located on an anterior portion of the subsequent inferior vertebra 92, but further to the anterior than the first center of rotation 94. In particular, the second center of rotation is located outside of the space 98 directly below the bearing component 24. This second center of rotation 96 is designed to provide a center of rotation for flexion/extension movement. Accordingly, during flexion/extension, the inferior plate 26 is designed to rotate upon the bearing component 24 with the convex articulating surface 52 of the inferior plate 26 engaging the concave inferior bearing surface 72 of the bearing component. This center of rotation 96 is consistent with current bio-medical analysis for the C5-C6 cervical functional unit.

The centers of rotation shown in FIG. 8 have been provided based on current data for the C5-C6 functional unit. However, for this functional unit, as well as other functional units, the first center of rotation 94 and second center of rotation 96 may be positioned in other locations consistent with updated findings from biomechanical analyses. For example, if it is determined that the lateral bending or axial rotation center of rotation for a particular functional unit should be located slightly to the posterior of a lateral midline, the prosthesis device 20 may be designed with the first center of rotation 94 closer to a central axis or slightly to the posterior of the central axis. At the same time, the second center of rotation 96 may remain significantly removed from the first center of rotation, such as in an anterior portion of the inferior vertebra as shown in FIG. 8.

Figure 9:
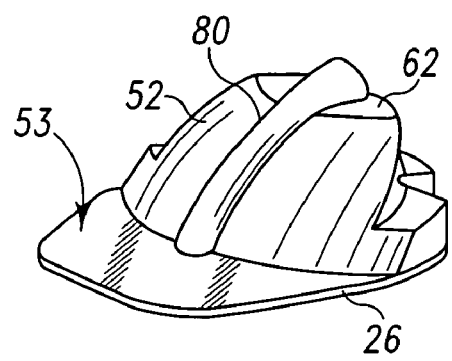
FIG. 9 shows a posterior perspective view of an inferior plate of an alternative embodiment of the disc prosthesis of FIG. 1.
Figure 10:
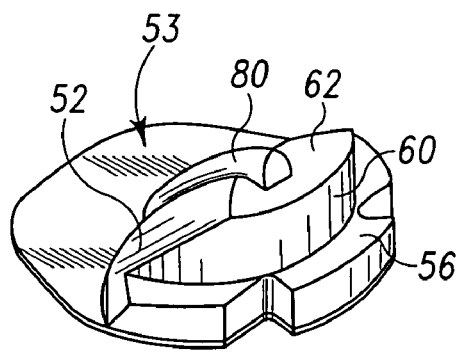
FIG. 10 shows an anterior perspective view of the inferior plate of FIG. 9.

An alternative embodiment of the intervertebral disc prosthesis is shown in FIGS. 9-12. As shown in FIGS. 9 and 10, in this embodiment, the inferior endplate 26 includes a rail 80 positioned upon and extending above the upper articulating surface 52 of the inferior endplate 26. The rail 80 extends radially along the center portion of the upper articulating surface 52. One end of the rail 80 terminates in the flat surface 53 located at the posterior portion of the inferior endplate 26. The opposite end of the rail 80 terminates above the upper platform 62 of the dome 60. The rail 80 has a generally semi-circular cross-section and provides a smooth track upon which the bearing component 24 can glide.

Figure 11:
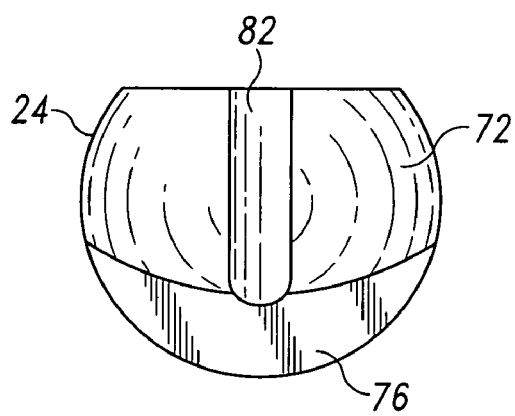
FIG. 11 shows a bottom view of a mobile bearing designed to mate with the inferior plate of FIG. 9.

FIG. 11 shows a groove 82 formed in the inferior bearing surface 72 of the bearing component 24. The groove 82 has a substantially semi-circular cross-section and cuts into the inferior bearing surface 72, providing an indentation that is congruent with the rail 80. The groove 82 extends radially along the inferior bearing surface 72 of the bearing component from the posterior flat shoulder 76 to an anterior portion of the bearing component.

Figure 12:
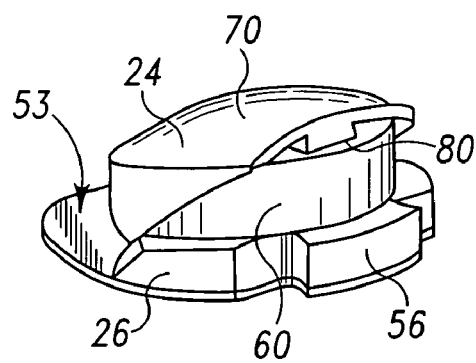
FIG. 12 shows an anterior perspective view of the inferior plate of FIG. 9 in engagement with the mobile bearing of FIG. 11.
Figure 13:
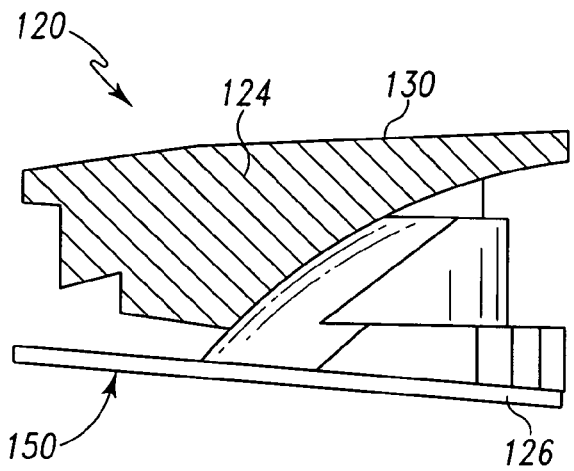
FIG. 13 shows a side view of a superior plate and an inferior plate of an alternative embodiment of the disc prosthesis of FIG. 1 with the superior plate shown in cross-section.
Figure 14:
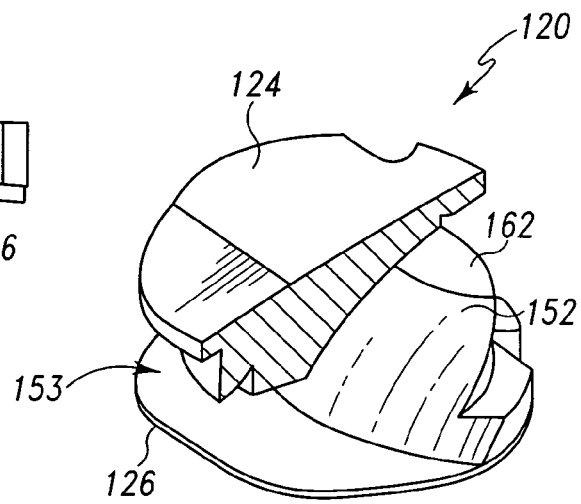
FIG. 14 shows an upper perspective view of the disc prosthesis of FIG. 13 with the superior plate in partial cross-section.
Figure 15:
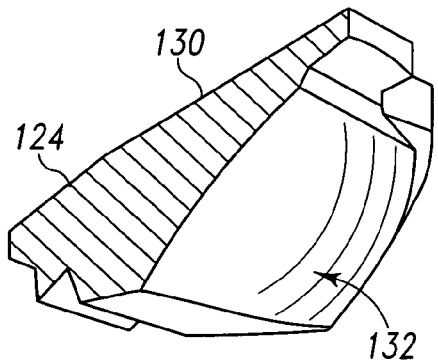
FIG. 15 shows a lower perspective view of the superior plate of the disc prosthesis of FIG. 13 with the superior plate in partial cross-section.
Figure 16:
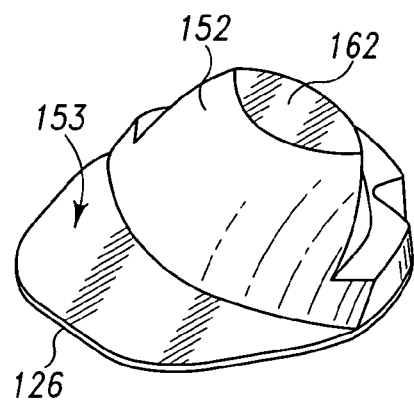
FIG. 16 shows an upper perspective view of the inferior plate of the disc prothesis of FIG. 13.

When the rail 80 is mated with the groove 82, as shown in FIG. 12, an articulating joint is formed that allows the bearing component 24 to rotate upon the inferior endplate 26. This articulating joint provides for flexion/extension movement with the groove 82 riding upon the rail 80. However, lateral bending and axial rotation movement is prohibited for this articulating joint, as the mating groove 80 and rail 82 lock the bearing component 24 in place to only allow rotation of the bearing component along the rail.

Accordingly, the embodiment, of FIGS. 9-12 incorporates a structural element that provides a means to lock a degree of freedom for the bearing component. In particular, the embodiment disclosed in FIGS. 9-12 comprises a bearing component with two articulating joints where one of the two articulating joints allows flexion/extension movement but restricts lateral bending and axial rotation movements. Advantageously, this arrangement is useful in preventing migration of the bearing component, as the intervertebral disc prosthesis is configured to provide more natural movement for the functional segmental unit.

With reference now to FIGS. 13-16, another alternative embodiment of the intervertebral disc prosthesis is shown. The intervertebral disc prosthesis 120 of FIGS. 13-16 comprises a superior endplate 122 and an inferior endplate 126. The superior endplate 122 includes an upper surface 130 configured to face a superior vertebra. Opposite the upper surface 130 is a lower articulating surface 132 (see FIG. 15). The lower articulating surface 132 is a generally spherical concave surface. The lower articulating surface 132 is designed and dimensioned to articulate against the inferior endplate 126.

The inferior endplate 126 includes a lower surface 150 configured to face an inferior vertebra. Opposite the lower surface 150 is an upper articulating surface 152. The upper articulating surface 152 is a generally spherical convex surface that is congruent with the lower articulating surface 132 of the superior endplate 122. The upper articulating surface 152 of the inferior endplate 126 is designed to engage and articulate against the lower articulating surface 132 of the superior endplate 122. A generally flat surface 153 is provided to the posterior of the upper articulating surface 152 on the inferior endplate 122. A flat upper platform 162 is provided to the anterior of the upper articulating surface 152.

The superior endplate 122 and inferior endplate 126 may be comprised of various materials as are known to those of skill in the art for prosthetic devices. For example, the superior and inferior endplates may be comprised of ceramic, metal, or any other combination of biocompatible materials with acceptable biological and mechanical properties.

In the embodiment of FIGS. 13-16, the dimension and location of the radius of both the concave lower articulating surface 132 and the convex upper articulating surface 152 is such that the instantaneous center of rotation at C5-C6 in flexion/extension is located at the anterior portion of the subsequent lower vertebra outside of the space immediately below the lower articulating surface 132, when viewed from above. Alternatively, the center of rotation may be positioned at any other location consequent with updated findings from biomechanical analyses.

In the embodiment of FIGS. 13-16, the intervertebral disc prosthesis 120 does not include a mobile bearing disc such as that disclosed in the previously described embodiments. While the usage of a mobile bearing disc has inherent advantages over other designs, under some circumstances it may be advantageous to provide a single, fixed bearing artificial cervical disc that places the instantaneous center of rotation in flexion/extension at the anterior portion of the subsequent lower vertebra.

In yet another single bearing embodiment not shown in the figures, the invention comprises a superior endplate, one fixed bearing core, and one inferior endplate. In this embodiment, the core is fixed to either the inferior endplate or the superior endplate and the other endplate is configured to rotate upon the core. In this embodiment, the superior endplate has a generally spherical, concave surface that articulates against the generally spherical, convex surface of the fixed bearing core. The dimension and location of the radius of both concave and convex surfaces is such that the instantaneous center of rotation at C5-C6 in flexion/extension is located at the anterior portion of the subsequent, lower vertebra, or any other location consequent with updated findings from biomechanical analyses with acceptable biological and mechanical properties. The fixed bearing component may be affixed to the inferior endplate by means of a locking mechanism such as a snap lock, adhesive, screws, or any of numerous other locking mechanisms known to those of skill in the art.

Materials for the endplates disclosed in the above paragraph, as well any endplates described herein may include cobalt chromium, titanium, stainless steel, or any other materials with acceptable biological and mechanical properties. The fixed bearing core, the mobile bearing core, or other bearing surfaces described herein may be made of ultra high weight polyethylene or numerous other materials with acceptable biological and mechanical properties as will be recognized by one of skill in the art.

When assembled and implanted in the patient, the intervertebral disc prosthesis disclosed herein provides an artificial disc having a plurality of instantaneous centers of rotation. The plurality of instantaneous centers of rotation are designed to facilitate different movements for the segmental unit where the prosthesis is implanted. As mentioned previously, with respect to the C5-C6 segmental unit, the radius of the inferior bearing surface provides an instantaneous center of rotation located outside of the disc space, when seen from above. Furthermore, the radius of the superior bearing surface provides an instantaneous center of rotation for lateral bending and axial rotation that is located approximately within the disc space, when seen from above, as normal, physiological motion requires. Of course, upon further discovery concerning the locus of the instantaneous location of the center of rotation in lateral bending, the upper, convex surface of the mobile bearing could be designed to target that specific location as well. In case the two center of rotation locations for lateral bending and axial rotation are mutually exclusive, the most important location for the center of rotation of the two motions (axial rotation or lateral bending) may be targeted.

Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. An intervertebral disc prosthesis configured for insertion between a superior vertebral body and an inferior vertebral body, the intervertebral disc prosthesis comprising:
   a first endplate including a first upper vertebra facing surface and a concave articulating surface;
   a second endplate including a second lower vertebra facing surface and a convex articulating surface; and
   a bearing component positioned between the first endplate and the second endplate, the bearing component including (i) a convex bearing surface configured to engage the concave articulating surface of the first endplate and (ii) a concave bearing surface configured to engage the convex articulating surface of the second endplate,
   wherein the concave bearing surface of the bearing component and the convex articulating surface of the second endplate form a first contact pair and define a flexion/extension center of rotation for the bearing component, and
   wherein, when the intervertebral prosthesis is viewed in a side cross-sectional view in which (i) the second lower vertebra facing surface defines a left lower plate end and a right lower plate end, (ii) a region in the cross-sectional view is defined between a first vertical plane tangent to the left lower plate end and a second vertical plane parallel to the first plane and tangent to the right lower plate end, (iii) an entire cross-section of the bearing component is located within the region, (iv) an entire cross-section of the concave bearing surface is directly beneath the first upper vertebra facing surface, and (v) an entire cross-section of the convex bearing surface is directly above the second lower vertebra facing surface, the flexion/extension center of rotation for the bearing component is outside of the region.

2. The intervertebral disc prosthesis of claim 1 wherein the bearing component and the second endplate are configured such that the flexion/extension center of rotation is located on an anterior portion of the inferior vertebral body when the intervertebral disc prosthesis is inserted.

3. The intervertebral disc prosthesis of claim 1 wherein the bearing component and the second endplate are configured such that the flexion/extension center of rotation is positioned along a first line passing through the center of a facet immediately superior to the intervertebral disc prosthesis, wherein the first line is substantially perpendicular to a second line, and wherein the second line also passes through the center of the facet and defines a facet angle when the intervertebral disc prosthesis is inserted.

4. The intervertebral disc prosthesis of claim 1 wherein the convex bearing surface of the bearing component and the concave bearing surface of the first endplate form a second contact pair and define a lateral bending/torsional center of rotation for the bearing component.

5. The intervertebral disc prosthesis of claim 4 wherein the lateral bending/torsional center of rotation is located directly below the convex bearing surface.

6. The intervertebral disc prosthesis of claim 1 further comprising a rail provided on the convex articulating surface of the second endplate and a groove provided on the concave bearing surface of the bearing component, wherein the rail engages the groove when the concave bearing surface of the bearing component engages the convex articulating surface of the second endplate.

7. An intervertebral disc prosthesis comprising:
   a superior component including a superior vertebra facing surface;
   an inferior component including an inferior vertebra facing surface; and
   an intermediate component positioned vertically between the superior vertebra facing surface and the inferior vertebra facing surface, the intermediate component including a superior bearing surface engaging the superior component and an inferior bearing surface engaging the inferior component, wherein the superior bearing surface defines a first center of rotation for the intermediate component and the inferior bearing surface defines a second center of rotation for the intermediate component, and wherein the first center of rotation is horizontally offset from the second center of rotation when the first and second centers of rotation are projected onto a first plane perpendicular to a vertical axis substantially perpendicular to the superior vertebra facing surface and the inferior vertebra facing surface, and wherein, when the intervertebral disc prosthesis is viewed in a side view, at least one of the projected first center of rotation and the projected second center of rotation is located outside of an area between a second plane perpendicular to the first plane and tangent to a left end of the superior component and a third plane perpendicular to the first plane, parallel to the second plane, and tangent to a right end of the superior component.

8. The intervertebral disc prosthesis of claim 7 wherein the first center of rotation is horizontally offset from the second center of rotation by a distance of at least 1 mm.

9. The intervertebral disc prosthesis of claim 7 wherein the superior bearing surface is convex.

10. The intervertebral disc prosthesis of claim 9 wherein the inferior bearing surface is concave.

11. The intervertebral disc prosthesis of claim 7 wherein the first center of rotation is offset from the second center of rotation by at least 5 mm.

12. The intervertebral disc prosthesis of claim 7 wherein the intermediate component engages the inferior component with a tongue-and-groove arrangement.

13. The intervertebral disc prosthesis of claim 12 wherein the tongue is provided on the inferior component and the groove is provided on the inferior bearing surface.

14. An intervertebral disc prosthesis designed for implantation between a superior vertebra and an inferior vertebra, the inferior vertebra including an anterior portion, the intervertebral disc prosthesis comprising:
 a superior vertebra facing surface;
 an inferior vertebra facing surface; and
 a bearing surface positioned between the superior vertebra facing surface and the inferior vertebra facing surface, the bearing surface configured to allow the superior vertebra facing surface to pivot relative to the inferior vertebra facing surface about a center of rotation, wherein, when the intervertebral prosthesis is viewed in a side cross-sectional view in which (i) the inferior vertebra facing surface defines a left lower end and a right lower end,(ii) a region in the cross-sectional view is defined between a first vertical plane tangent to the left lower end and a second vertical plane parallel to the first plane and tangent to the right lower end, (iii) an entire cross-section of the bearing surface is located within the region, (iv) an uppermost point of the entire cross-section of the bearing surface is lower than the entire superior vertebra facing surface, and (v) a lowest point of the entire cross-section of the bearing surface is higher than the entire inferior vertebra facing surface, the center of rotation is located outside of the region.

15. The intervertebral disc prosthesis of claim 14 wherein the bearing surface is provided on a superior component along with the superior vertebra facing surface.

16. The intervertebral disc prosthesis of claim 14 further comprising a superior component wherein the bearing surface is provided on an intermediate component separate from the superior component, the superior component comprising the superior vertebra facing surface.

17. The intervertebral disc prosthesis of claim 16 further comprising an inferior component wherein the inferior component further comprises an inferior articulating surface configured to engage the bearing surface of the intermediate component.

18. The intervertebral disc prosthesis of claim 17 wherein the inferior articulating surface engages the bearing surface of the intermediate component with a tongue-and-groove arrangement.

19. The intervertebral disc prosthesis of claim 17 wherein the bearing surface of the intermediate component is concave and the articulating surface of the inferior component is convex.

20. The intervertebral disc prosthesis of claim 14 wherein the center of rotation is configured to be located to the anterior of the inferior vertebra when the intervertebral disc prosthesis is implanted.

* * * * *